US 12,232,899 B2

(12) United States Patent
Li et al.

(10) Patent No.: US 12,232,899 B2
(45) Date of Patent: Feb. 25, 2025

(54) PORTABLE THREE-DIMENSIONAL DIGITAL RADIOGRAPHY (DR) SYSTEM

(71) Applicant: Shenzhen Browiner Tech Co., Ltd, Shenzhen (CN)

(72) Inventors: Shufeng Li, Shenzhen (CN); Anshan Wang, Shenzhen (CN); Xiaolei Li, Shenzhen (CN)

(73) Assignee: Shenzhen Browiner Tech Co., Ltd, Shenzhen (CN)

( * ) Notice: Subject to any disclaimer, the term of this patent is extended or adjusted under 35 U.S.C. 154(b) by 199 days.

(21) Appl. No.: 17/979,242

(22) Filed: Nov. 2, 2022

(65) Prior Publication Data

US 2023/0210485 A1 Jul. 6, 2023

(30) Foreign Application Priority Data

Jan. 6, 2022 (CN) .......................... 202210007624.0

(51) Int. Cl.
  *A61B 6/40* (2024.01)
  *A61B 6/00* (2006.01)
  *G01T 7/00* (2006.01)

(52) U.S. Cl.
  CPC .......... *A61B 6/4452* (2013.01); *A61B 6/4405* (2013.01); *G01T 7/00* (2013.01)

(58) Field of Classification Search
  CPC ........ A61B 6/4452; A61B 6/4405; G01T 7/00
  See application file for complete search history.

(56) References Cited

U.S. PATENT DOCUMENTS

| 2012/0106705 | A1* | 5/2012 | Mikami | A61B 6/4233 378/70 |
| 2015/0010126 | A1* | 1/2015 | Rotondo | A61B 6/032 378/19 |
| 2016/0029984 | A1* | 2/2016 | Jang | A61B 6/56 378/189 |
| 2018/0008216 | A1* | 1/2018 | Kim | A61B 6/4452 |

(Continued)

FOREIGN PATENT DOCUMENTS

| CN | 209645070 U | 11/2019 |
| CN | 210381073 U | 4/2020 |

(Continued)

OTHER PUBLICATIONS

First Office Action issued in counterpart Chinese Patent Application No. 202210007624.0, dated Feb. 16, 2022.

(Continued)

*Primary Examiner* — Hugh Maupin
(74) *Attorney, Agent, or Firm* — Westbridge IP LLC

(57) ABSTRACT

Disclosed is a portable three-dimensional DR system. The portable three-dimensional DR system includes a support mechanism, an X-ray generator, a stand and a flat panel detector. The support mechanism includes a support tube, a transmission component, a drive component and a support pole slidingly provided in the support tube. The X-ray generator is detachably provided on the support pole, the transmission component is used for driving the X-ray generator to move in the direction of closing to or far from the support tube, the drive component is used for driving the X-ray generator to rotate, the flat panel detector is provided on the stand, and the stand is placed on a horizontal plane.

8 Claims, 11 Drawing Sheets

(56) References Cited

U.S. PATENT DOCUMENTS

| | | | |
|---|---|---|---|
| 2019/0139244 A1* | 5/2019 | Pras | .......................... G06T 7/55 |
| 2020/0000426 A1 | 1/2020 | Simon et al. | |
| 2020/0163634 A1 | 5/2020 | Turner et al. | |

FOREIGN PATENT DOCUMENTS

| | | | |
|---|---|---|---|
| CN | 210424372 | U | 4/2020 |
| CN | 210742163 | U | 6/2020 |
| CN | 111578062 | A | 8/2020 |
| CN | 112261249 | A | 1/2021 |
| CN | 214434254 | U | 10/2021 |
| CN | 214663480 | U | 11/2021 |
| WO | 2013074032 | A1 | 5/2013 |

OTHER PUBLICATIONS

Extended European Search Report issued in counterpart European Patent Application No. 22205803.4, dated May 12, 2023.

* cited by examiner

D-D

PORTABLE THREE-DIMENSIONAL DIGITAL RADIOGRAPHY (DR) SYSTEM

CROSS-REFERENCE TO RELATED APPLICATIONS

This application claims priority to the Chinese Patent Application No. 202210007624.0, filed on Jan. 6, 2022, the entire contents of which are incorporated herein by reference.

TECHNICAL FIELD

The present disclosure relates to the technical field of three-dimensional digital radiography (DR), and in particular to a portable three-dimensional DR system.

BACKGROUND

Three-dimensional DR mainly includes an X-ray generator, a flat panel detector and an image process workstation. Three-dimensional DR can be applied in the medical field, three-dimensional DR technology can provide reconstruction images or image groups of the scanned patient's tomography. The reconstructed image or image group includes all the image information in the three-dimensional space of the scanned area of the patient, the doctor can acquire the patient's tomography, sagittal section, coronal section or information of any point of the three-dimensional space to assist the diagnosis. Besides, the three-dimensional DR can also be supplied in the archaeology field to provide a three-dimension image of the relic for acquiring a more specific information, thus the three-dimensional DR has a wide range of applications in the field of fluoroscopy, spot film photography and various kinds of angiography.

In the related technologies, when the patient, relic or other stuff need a scanning imaging, the scanned objects are sent to the three-dimensional DR device for a three-dimensional scanning imaging. While some of the relics cannot be moved, so that instead of being sent to the three-dimensional DR device for a three-dimensional scanning imaging, the relics can just be simply captured for observation. Besides, when the doctor goes to the countryside to diagnose and treat patients or goes to the disaster area to support, some patients are in serious condition, and cannot be transferred to the three-dimensional DR device for three-dimensional imaging to observe the condition, which is not convenient for doctors to make timely treatment.

In terms of the above related technologies, the inventor think that the existing three-dimensional DR device cannot be moved freely, and there are many inconvenient situations when diagnosing and treating patients or scanning other objects. Therefore, it is necessary to design a portable three-dimensional DR system.

SUMMARY

In order to improve the portability of the three-dimensional DR system, the present disclosure aims to provide a portable three-dimensional DR system.

The present disclosure provides a portable three-dimensional DR system.

The portable three-dimensional DR system includes a support mechanism, an X-ray generator, a stand and a flat panel detector, the support mechanism includes a support tube, a transmission component, a drive component and a support pole slidingly provided in the support tube, the X-ray generator is detachably provided on the support pole, the transmission component is used for driving the X-ray generator to move in the direction of closing to or far from the support tube, the drive component is used for driving the X-ray generator to rotate, the flat panel detector is provided on the stand, and the stand is placed on a horizontal plane.

By adopting the above technical solution, when using the portable three-dimensional DR system, firstly the support pole is pulled out from the support tube, then the X-ray generator is connected to the support pole, and then the stand is placed on the horizontal plane, the flat panel detector is connected to the stand, the scanned object is placed on the side of the flat panel detector, then the transmission component is started to drive the X-ray generator to rotate, so that the object is scanned and photographed, when after used, firstly the X-ray generator is detached from the support pole and the support pole is telescoped into the support tube to be stored, which is convenient to be taken away and the portability of the three-dimensional DR system is improved.

In an embodiment, the transmission component includes: a transmission motor provided in the support pole; a transmission gear; and a transmission rack provided on an inner wall of support tube, and the transmission motor is connected with the transmission gear, the transmission rack is provided in a length direction of the support tube, the transmission gear is engaged with the transmission rack to drive the support pole to slide in the support tube, and one end of the support pole far from the support tube is connected with a mounting platform for mounting the X-ray generator, and the mounting platform is detachably connected with the support tube.

By adopting the above technical solution, when using the portable three-dimensional DR system, the transmission motor is started, the transmission rack is driven through the transmission motor to rotate, the transmission gear is engaged with the transmission rack, and the transmission gear can be moved on the transmission rack, so that the support pole can be moved along the arranging direction of transmission rack to drive the X-ray generator to move, besides, when after used, the X-ray generator is detached from the mounting platform, then the support pole is telescoped in the support tube, the mounting platform can be connected with the support tube to protect the support tube, and to avoid the object falling into the support tube, which improves the safety.

In an embodiment, the support tube includes a first support tube and a second support tube, the first support pole is slidingly provided in the second support tube, the support pole is a telescopic pole and is slidingly provided in the first support tube, the transmission rack comprises a first rack provided on an inner wall of the first support tube and a second rack provided on an inner wall of the second support tube, and the first rack and the second rack are spliced with each other.

By adopting the above technical solution, when storing the portable three-dimensional DR system, the first support tube is slidingly provided in the second support tube, then the support pole is telescoped in the first support tube, so that the support tube can be stored for several times, which improves the space utilization.

In an embodiment, a sliding slot is provided on the first support tube, a magnetic plate is provided on the first support tube, the second rack is provided in the sliding slot and magnetically connected with the magnetic plate; and an outer wall of the first support tube is provided with a plurality of position balls, an inner wall of the second support tube is provided with a position hole for containing the position ball and a position slot, the position ball is provided in the position slot and slidingly connected with the second support tube.

By adopting the above technical solution, when using the portable three-dimensional DR system, the first support tube is pulled out and then rotated, the position ball is placed in the position hole, the first rack is spliced with the second rack, when storing the portable three-dimensional DR system, firstly the first rack is rotated, then the position ball is placed in the position slot, then the first support tube is telescoped into the second support tube, the second rack is magnetically connected with the magnetic beam by being provided in the sliding slot, the provision of the position ball plays a role in positioning and fixing, so that the first rack and the second rack is spliced more accurate and more stable.

In an embodiment, a mounting box is detachably connected on the mounting platform, and a containing slot is provided on the mounting box, and a mounting cover for opening or closing the containing slot is further provided on the mounting box, and the X-ray generator is provided in the containing slot and rotatably connected with the mounting box, and the drive component includes: a rotary wheel; and a drive motor provided on the mounting box for driving the rotary wheel to rotate; and the rotary wheel is configured to drive the X-ray generator to rotate.

By adopting the above technical solution, when using the portable three-dimensional DR system, the drive motor is driven, the drive motor will drive the rotary wheels on two sides of the X-ray generator to rotate the X-ray generator, simultaneous driving of the two sides improves the rotation stability of the X-ray generator, besides, the X-ray generator is provided in the mounting box, when after used, the X-ray generator is rotated to be placed in the containing slot, then the mounting cover is closed to cover the containing slot, the X-ray generator is placed in the mounting box, which reduces the crash of the X-ray generator during transportation.

In an embodiment, an inner wall of the support tube is rotatably provided with a rotary panel, and a rotary hole is provided on the rotary panel, one end of the support pole is rotatably connected with an adjusting pole, and the adjusting pole is threadedly connected with the rotary panel through a rotary hole, and the transmission component includes: a transmission motor provided on the support tube, and an output shaft of the transmission motor is concentrically connected with a first bevel gear, the rotary panel is connected with a second bevel gear, and the first bevel gear is engaged with the second bevel gear.

By adopting the above technical solution, when using the portable three-dimensional DR system, the worker can remotely control the transmission motor to rotate, the transmission motor drives the first bevel gear to rotate, the first bevel gear is engaged with the second bevel gear, the second bevel gear is rotated to drive the rotary panel to rotate, then the rotary panel is rotated so that the adjusting pole can drive the support pole to move in the support tube, which improves a space utilization.

In an embodiment, the support tube is further provided with a support component, and the support component includes a support body, a first roller, a connecting plate and a support bar, and the support body is connected with an end of the support pole, the first roller is rotatably connected with the support body, the support beam is connected with the support body, and an end of the support bar is rotatably connected with the connecting plate, and another end of the support bar is rotatably connected with a second roller, and a locking piece for locking up the second roller is provided on the support bar.

By adopting the above technical solution, the connecting plate is connected to the support body, the support bar is hinged with the support body, when the position of the three-dimensional DR system needs to be adjusted, the support tube can directly be pushed, the whole three-dimensional DR system can be moved under the effect of the first roller and the second roller, then the second roller is locked through the locking piece, so that the three-dimensional DR system is convenient to be moved, besides, when the three-dimensional DR system is used, the support bar can be waved in the direction of closing to the support tube, which is convenient to store the three-dimensional DR system, so that the three-dimensional DR system is portable.

In an embodiment, the stand includes a stand body, a plurality of telescopic feet and an adjusting component, one end of the telescopic foot is hinged with the stand body, and another end of the telescopic foot is placed on a horizontal plane, the adjusting component includes a moving pole, a rotary pole and a rotary gear, and the rotary pole is rotatably connected with the stand body, one end of the rotary pole is connected with the rotary gear, and a moving rack is provided on the moving pole, the rotary gear is engaged with the moving rack, and an adjusting hole is provided on the stand body, one end of the moving pole is slidingly connected with the stand body through the adjusting hole, and both ends of the moving pole are provided with baffles being parallel to each other, and one of the baffles is slidingly connected with the moving pole, and the baffle is used for clamping the flat panel detector.

By adopting the above technical solution, when using the portable three-dimensional DR system, firstly the telescopic foot is extended and placed on the horizontal plane to support the stand body, then the flat panel detector is placed between the two baffles so that the baffle is convenient to fix the flat panel detector, when the height of the flat panel detector needs to be adjusted, the rotary pole can be rotated to rotate the rotary gear, and the moving pole is driven to slide on the stand body to adjust the height of the flat panel detector, and the scope of application is improved, besides, the telescopic foot can be telescoped, which is convenient to be stored.

In an embodiment, the stand includes a mounting tube, a mounting pole, a mounting panel and a plurality of support-protection bars, the mounting pole is slidingly provided in the mounting tube, a fixing ring is slidingly provided on the mounting pole, and the flat panel detector is detachably connected with the fixing ring, one end of the mounting tube far from the flat panel detector is connected with the mounting panel, the mounting panel is rotatably connected with an end of the support-protection bar, and another end of the support-protection bar is rotatably connected with a caster.

By adopting the above technical solution, when after use, the flat panel detector is detached from the fixing ring for a separate storage, then the mounting pole is telescoped in the mounting tube, and the support-protection bar is rotated in a direction close to the mounting tube for facilitating the three-dimensional system to be stored after use, so as to facilitate the carriage of the three-dimensional DR system.

In conclusion, the present disclosure includes at least one of the following beneficial technical effects:

1. Firstly, the X-ray generator is detached from the support pole, and then the support pole is telescoped into the support tube for storage, which is easy to take away, and improve the portability of the three-dimensional DR system.

2. In terms of the storage, firstly the first support tube is slidingly provided in the second support tube, and the support pole is telescoped into the first support tube, which improves space utilization.

3. When after use, the X-ray generator is rotated to be placed in the containing slot, then the mounting cover is covered on the containing slot, the X-ray generator is in the mounting box, which reduces a crash condition of the X-ray generator during the transportation.

DETAILED DESCRIPTION OF THE EMBODIMENTS

The present disclosure will be further specifically described with reference to the accompanying drawings.

The embodiments of the present disclosure provide a portable three-dimensional DR system.

Embodiment 1

Figure 1:
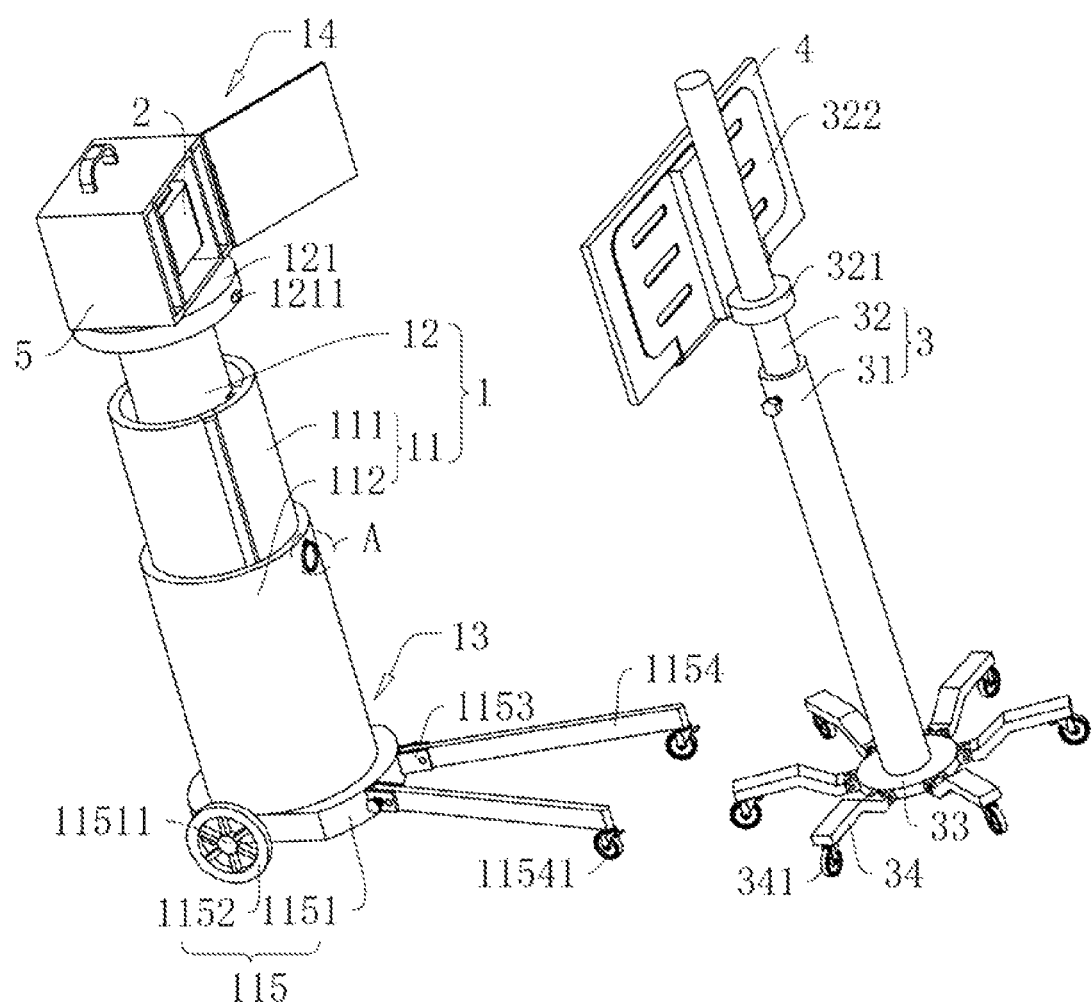
FIG. 1 is a schematic overall structural view of a portable three-dimensional DR system according to embodiment 1 of the present disclosure.

As shown in FIG. 1, the portable three-dimensional DR system includes a support mechanism 1, an X-ray generator 2, a stand 3 and a flat panel detector 4. The support mechanism 1 includes a support pole 12 and a support tube 11, and the support pole 12 is slidingly provided in the support tube 11, sliding in a length direction of the support tube 11. The X-ray generator 2 is provided on the support pole 12, the stand 3 is placed on a horizontal plane, and the flat panel detector 4 is provided on the stand 3. The support mechanism further includes a transmission component 13 and a drive component 14, the transmission component 13 is used for driving the X-ray generator 2 to move towards or away from the support tube 11, the drive component 14 is used for driving the X-ray generator 2 to rotate, which is convenient to scan and photograph the object.

The support tube 11 includes a first support tube 111 and a second support tube 112, and both the first support tube 111 and the second support tube 112 of this embodiment are circular structure. The outer diameter of the first support tube 111 is smaller than the inner diameter of the second support tube 112, and the first support tube 111 is slidingly provided in the second support tube 112. The support pole 12 of this embodiment is a telescopic pole, and one end of the support pole 12 is slidingly provided in the first support tube 111, and another end of the support pole 12 is connected with a mounting platform 121 through a screw, a side of the mounting platform 121 far from the support pole 12 is detachably connected with the X-ray generator.

Figure 2:
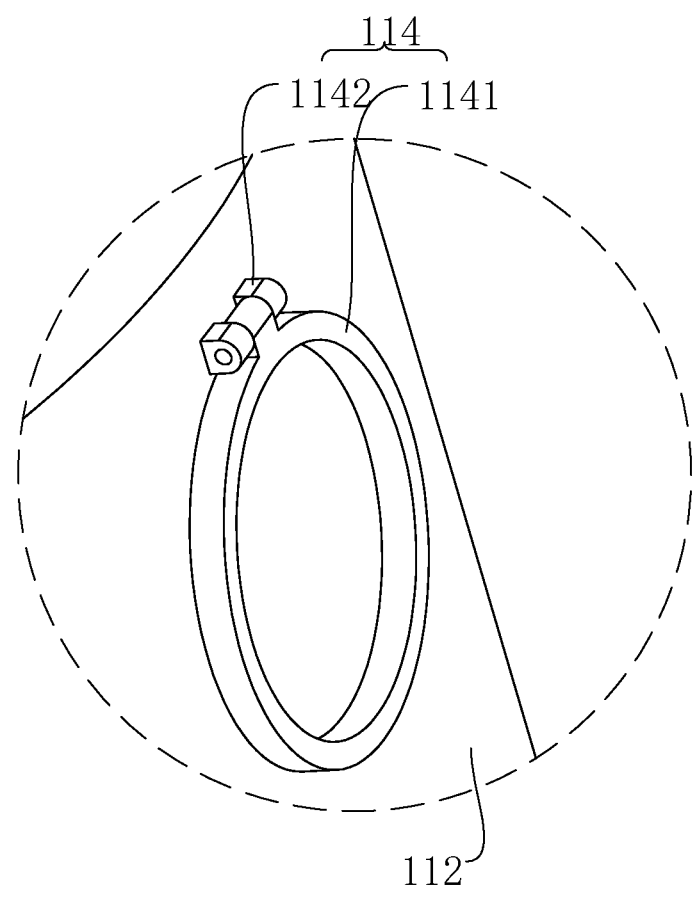
FIG. 2 is an enlarged schematic view at portion A in FIG. 1.

As shown in FIG. 1 and FIG. 2, a plurality of protrusions 1211 are integrally formed on a sidewall of the mounting platform 121, the quantity of the protrusion 1211 in this embodiment is two, and the two protrusions are oppositely arranged on the two sides of the mounting platform 121. An outer wall of the second support tube 112 close to the mounting platform 121 is provided with a fastening component 114, the fastening component 114 includes a fastening bar 1142 and a fastening ring 1141, the fastening bar 1142 is connected with the second support tube 112 through a screw, and the fastening ring 1141 is hinged with the fastening bar 1142. A limiting slot is provided on the protrusion 1211, the fastening ring 1141 is provided in the limiting slot and fastened with the protrusion 1211. The fastening component 114 is used for fixing the mounting platform 121 on the second support tube 112.

Figure 3:
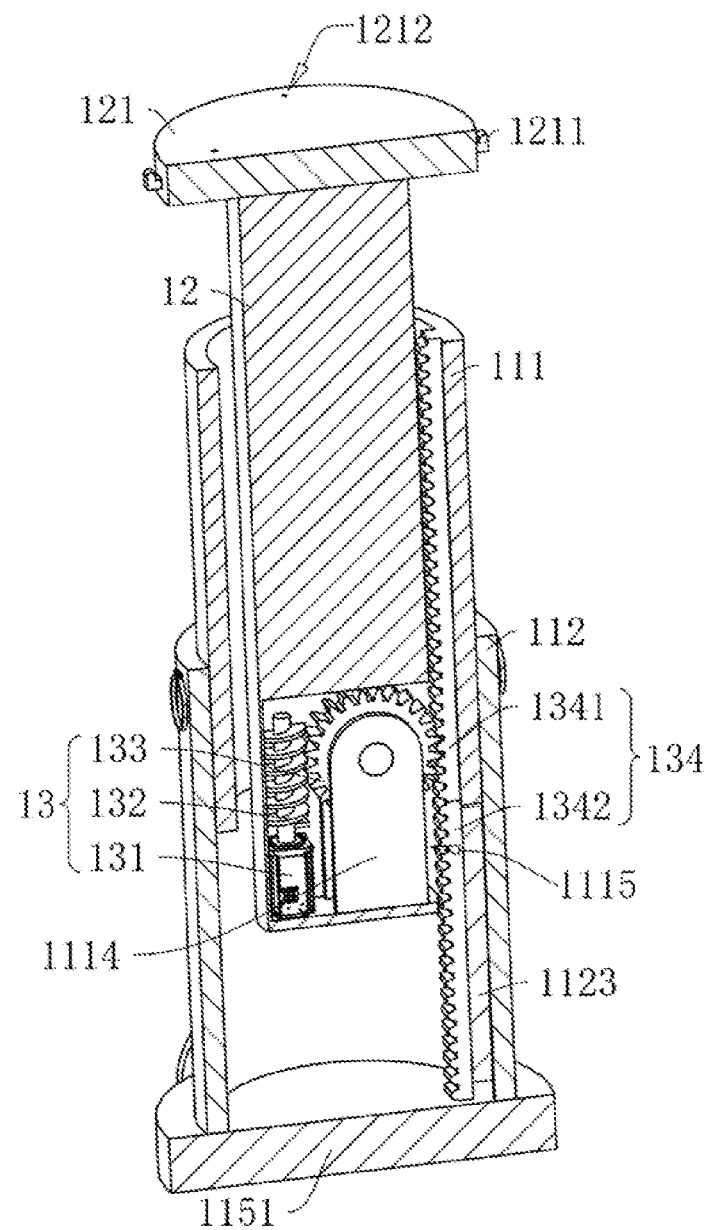
FIG. 3 is a schematic section view of the portable three-dimensional DR system according to embodiment 1 of the present disclosure.

As shown in FIG. 3, the transmission component 13 includes a transmission rack 134, the transmission rack 134 includes a first rack 1341 and a second rack 1342, the first rack 1341 is provided in the first support tube 111, this embodiment is in a screw connection. A side of the second rack 1342 is connected with a connecting rack 1123, a side of the connecting rack 1123 far from the second rack 1342 is connected with an inner wall of the second support tube 112, this embodiment is in a screw connection. The first rack 1341 and the second rack 1342 are provided in a same direction with the sliding direction of the support pole 12, and the first rack 1341 and the second rack 1342 are joined together on the side adjacent to each other.

Figure 4:
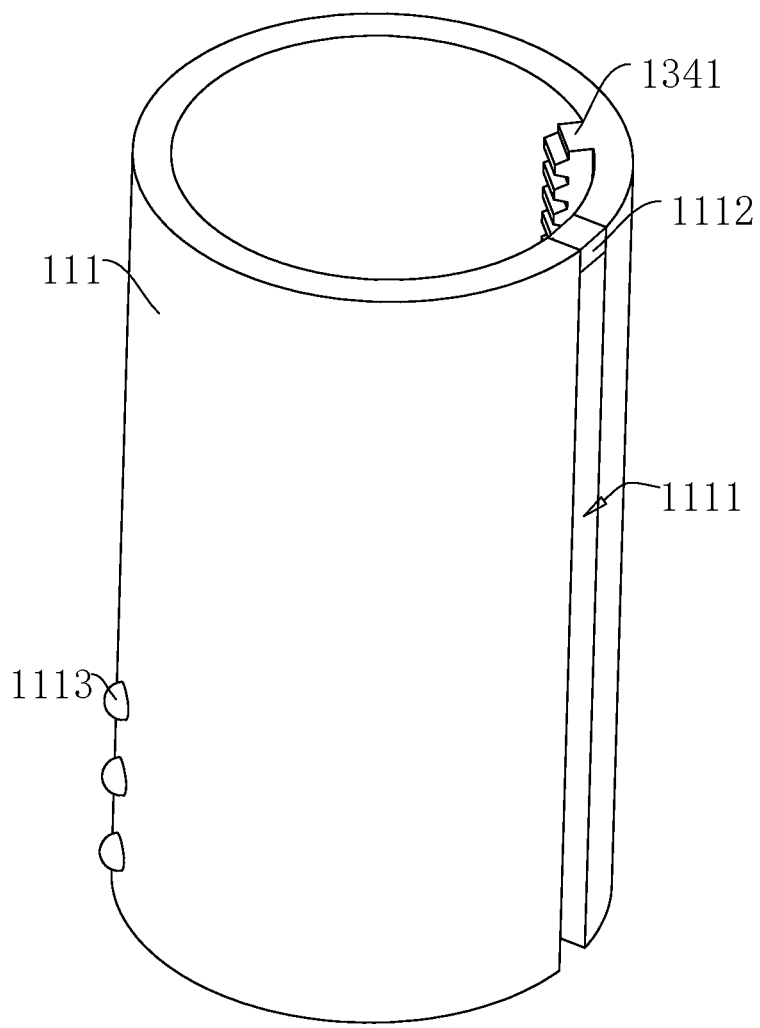
FIG. 4 is a schematic overall structural view of a first support tube of the portable three-dimensional DR system according to embodiment 1 of the present disclosure.

As shown in FIG. 3 and FIG. 4, a sliding slot 1111 is provided on the first support tube 111, a magnetic plate 1112 is integrally formed on the first support tube 111, and the second rack 1342 is provided in the sliding slot 1111 and magnetically connected with the magnetic plate 1112. A plurality of position balls 1113 are integrally formed on an outer wall of the first support tube 111, and the position ball 1113 is sequentially provided along the length direction of the first support tube 111.

Figure 5:
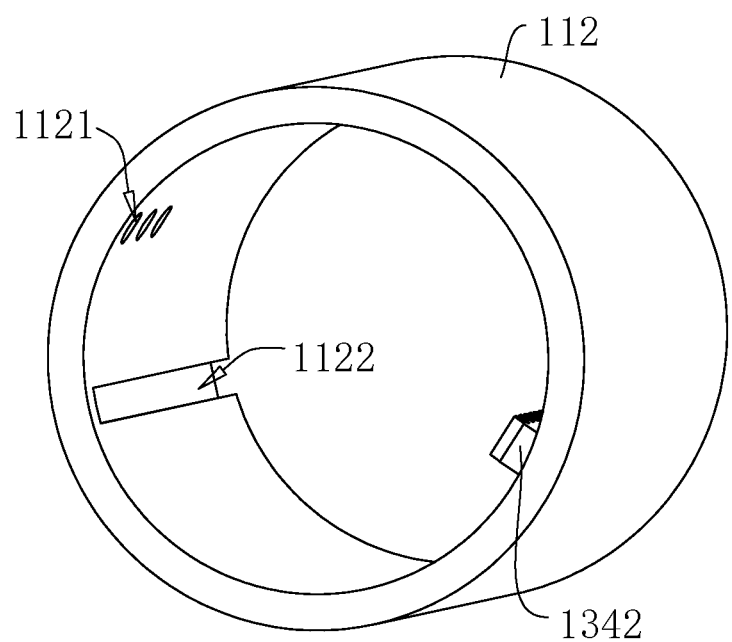
FIG. 5 is a schematic overall structural view of a second support tube of the portable three-dimensional DR system according to embodiment 1 of the present disclosure.

As shown in FIG. 4 and FIG. 5, the inner wall of the second support tube 112 is further provided with a position slot 1122 and a position hole 1121 corresponding to the position 1113. When using the portable three-dimensional DR system, the position ball 1113 is in the position slot 1122, then the first support tube 111 is pulled out from the second support tube 112, and then the first support tube 111 is rotated to place the position ball 1113 in the position hole, then the first rack 1341 is spliced with the second rack 1342. When storing the portable three-dimensional DR system, the first support tube 111 is rotated again to place the 30) position ball 1113 in the position slot 1122, so that the first support tube 111 is pushed into the second support tube for a storage, at the moment, the second rack 1342 is in the sliding slot 1111 and magnetically connected with the magnetic plate 1112, the provision of the position ball 1113 is effective on positioning and fixing so that the first rack 1341 and the second rack 1342 are spliced more accurate and stable.

As shown in FIG. 3, the transmission component 13 further includes a transmission motor 131, a worm 132 and a transmission gear 133, the transmission gear 133 of this embodiment is a worm gear. The transmission motor 131 is provided in the support pole 12, this embodiment is in a screw connection, the transmission motor 131 is connected with the worm 132, and the worm 132 is provided in the length direction of the support pole 12. The transmission gear 133 is rotatably provided in the support pole 12 through a mounting frame 1114, and the mounting frame 1114 is connected with the support pole 12 through a screw. An abdication slot 1115 is further provided on the support pole 12, a side of the transmission gear 133 is engaged with a worm gear, and another side of the transmission gear 133 is engaged with the rack through the abdication slot 1115.

As shown in FIG. 1, a side of the second support tube 112 far from the mounting platform 121 is provided with a support component, the support component 115 includes a support body 1151, a roll bar 11511 and a first roller 1152. In this embodiment, the support component 115 includes two first rollers 1152. An end of the roll bar 11511 is connected with the first roller 1152 through the screw, another end of the roll bar 11511 passes through the support body 1151 and is connected with another first roller 1152 through the screw. The support component 115 further includes a connecting plate 1153 and a support bar 1154, an end of the connecting plate 1153 is connected with the support body 1151 through the screw, another end of the connecting plate 1153 is hinged with an end of the support bar 1154, and another end of the support bar 1154 is rotatably connected with a second roller 11541, the support bar 1154 can be rotated in a direction of closing to the second support tube 112, so that the support bar 1154 is easy to be folded and stored. The support bar 1154 is further provided with a locking piece for locking up the second roller 11541, and the quantity of the connecting panel 1153 is two.

Figure 6:
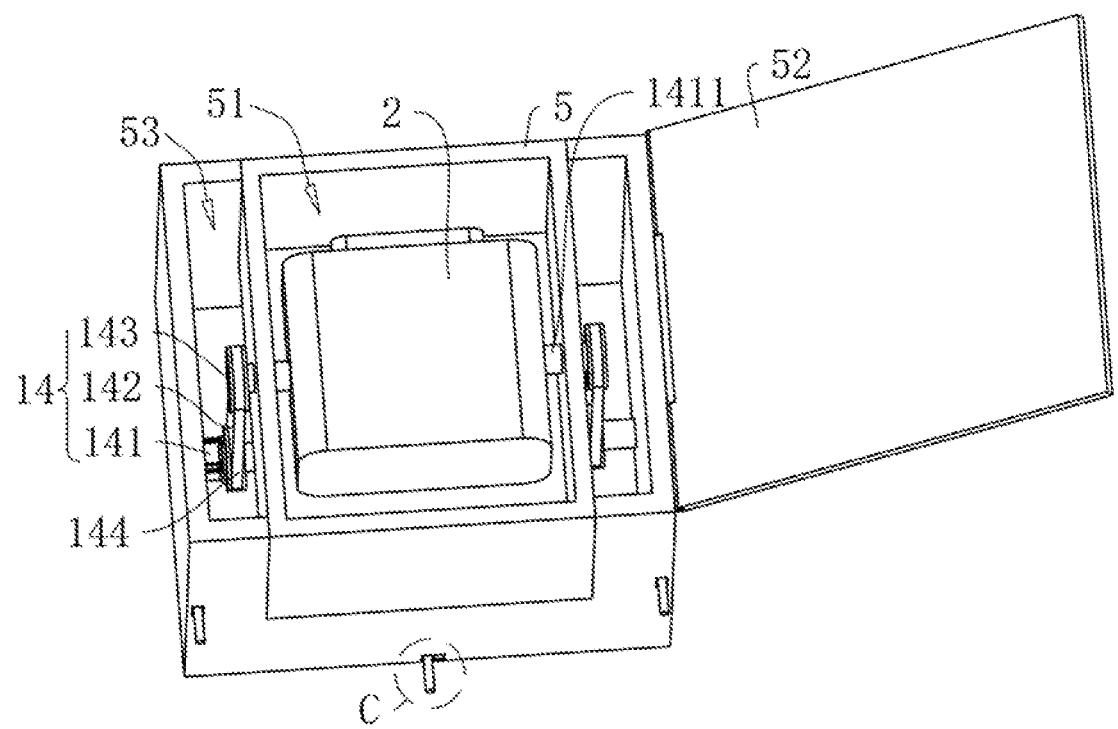
FIG. 6 is a schematic overall structural view of the mounting box of the portable three-dimensional DR system according to embodiment 1 of the present disclosure.
Figure 7:
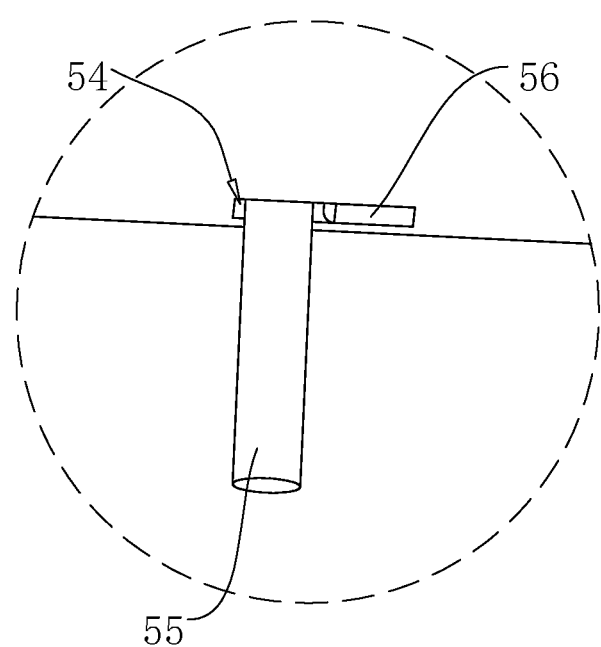
FIG. 7 is an enlarged schematic view at portion C in FIG. 6.

As shown in FIG. 6 and FIG. 7, a side of the mounting platform 121 far from the support pole 12 is detachably connected with a mounting box 5, and a side of the mounting box 5 towards the mounting platform 121 is provided with a plurality of through holes 54, the quantity of the through holes 54 are three, and the through holes 54 are evenly distributed on the mounting box 5. The inside of the through hole 54 is further slidingly provided with a locking pin 55, the mounting box 5 is hinged with a cover 56 for opening or closing the through hole 54, and an end of the locking pin 55 is attached with the cover 56.

As shown in FIG. 3 and FIG. 7, a side of the mounting platform 121 far from the support pole 12 is correspondingly provided with a lock hole 1212, the mounting box 5 is detachably connected with the mounting platform 121 through the locking pin 55 being slidingly provided in the lock hole 1212.

As shown in FIG. 6, a containing slot 51 is further provided on the mounting box 5, and the mounting box 5 is further hinged with a mounting cover 52 for opening or closing the containing slot 51. The X-ray generator 2 is provided in the containing slot and rotatably connected with the mounting box 5. The sidewall of the mounting box 5 is further provided with an interlayer 53, the drive component 14 includes a drive motor 141 and a rotary wheel 143, the drive motor 141 is provided in the interlayer 53 and connected with the mounting box 5, this embodiment is in a screw connection. Both two sides of the X-ray generator are passed through the sidewall of the containing slot 51 through a connecting pole to be connected with the rotary wheel 143, the rotary wheel 143 is rotatably connected with the sidewall of the containing slot 51. The drive motor 141 is connected with a drive pole 1411, the drive pole 1411 is connected with two driving wheels 142 through the screw, and an end of the driving pole 1411 far from the drive motor 141 is rotatably connected with a sidewall of the interlayer 53. One of the driving wheel 142 is rotatably connected with one of the rotary wheel 143 through a belt 144, another driving wheel 142 is rotatably connected with another rotary wheel 143 through the belt 144, when the drive motor 141 starts, the two rotary wheels 143 are driven to rotate simultaneously, so that two sides of the X-ray generator 2 is driven to rotate in the mounting box 5, which improves the space utilization and the rotation stability of the X-ray generator 2, and the drive component 14 is provided in the interlayer 53 of the mounting box 5, so that the portable three-dimensional DR system is more convenient to use. Besides, the mounting cover 52 can close the containing slot 51, which plays a role in protecting the X-ray generator 2, when get crashed, the damage to the X-ray generator is lowered.

As shown in FIG. 1, the stand 3 includes a mounting tube 31 and a mounting pole 32, and the mounting pole 32 is slidingly provided in the mounting tube 31, so that the mounting pole 32 is convenient to be stored in the mounting tube 31. An end of the mounting pole 32 far from the mounting tube 31 is provided with a fixing ring 321, and the fixing ring 321 can be slid on the mounting pole 32, and the fixing ring 321 is further provided with a locking screw for locking the sliding distance of the fixing ring 321. The fixing ring 321 is connected with a placing panel 322, when after use, the placing panel 322 can be detached from the fixing ring 321 by rotating the screw, which is portable.

An end of the mounting tube 31 far from the mounting pole 32 is connected with a mounting panel 33 through the screw, the mounting panel 33 of this embodiment is circular. A plurality of support-protection bars 34 are rotatably connected in a circumferential direction of the mounting panel 33, the quantity of the support-protection bar of this embodiment is six, and the plurality of support-protection bars 34 are evenly distributed in the circumferential direction of the mounting panel 33 and can be rotated in the direction of closing to the mounting tube 31. An end of the support-protection pole 34 far from the mounting panel 33 is further rotatably connected with a caster 341, which is convenient to adjust a direction of the stand 3.

The implementation principle of embodiment 1 is: when using the portable three-dimensional DR system, the fastening ring 1141 is opened, and the mounting platform 121 is held and pulled up to extend the support pole 12, the first support tube 111 is pulled up, and the first support tube 111 is rotated to place the position ball 1113 in the position hole 1121, then the first rack 1341 and the second rack 1342 are spliced; then the cover 56 of the mounting box 5 is opened to place the locking pin 55 in the locking hole 1212, the mounting box 5 is connected to the mounting platform 121 and the mounting cover 52 is opened, then the position of the X-ray generator is adjusted, so that the object or the human body is convenient to be scanned and photographed.

The support-protection pole 34 of the mounting tube 31 is rotated to land the caster 341, then the mounting pole 32 is pulled out from the mounting tube 31, the placing panel 322 is fixed on the fixing ring 321, the position of fixing ring 321 on the mounting pole 32 is adjusted to improve the scope of application, then the flat panel detector 4 is placed on the placing 322.

Lastly, the human body or the object is placed in front of the flat panel detector 4, then the transmission motor 131 is controlled through a computer to rotate by a worker so that the transmission gear 133 is rotated, the transmission gear 133 is engaged with the transmission rack 134, the support pole 12 can be moved repeatedly in the length direction of the transmission rack 134, at the same time, the X-ray generator 2 can be driven by the support pole 12 to move repeatedly in the direction of closing to the first support tube 111 or far from the first support tube 111, meanwhile, the drive motor 141 is started, the rotary wheels 143 on the two sides of the X-ray generator 2 are driven by the drive motor 141, so that the two sides of the X-ray generator 2 can be driven to rotate simultaneously, then the human body or the object is convenient to be scanned and photographed.

Embodiment 2

Figure 8:
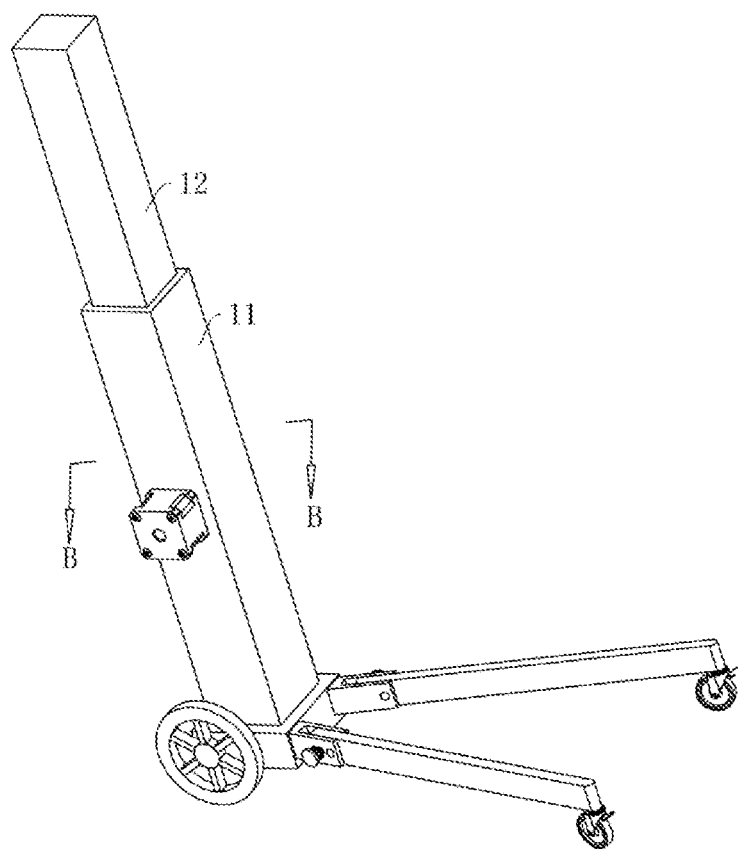
FIG. 8 is a schematic partial structural view of the portable three-dimensional DR system according to embodiment 2 of the present disclosure.
Figure 9:
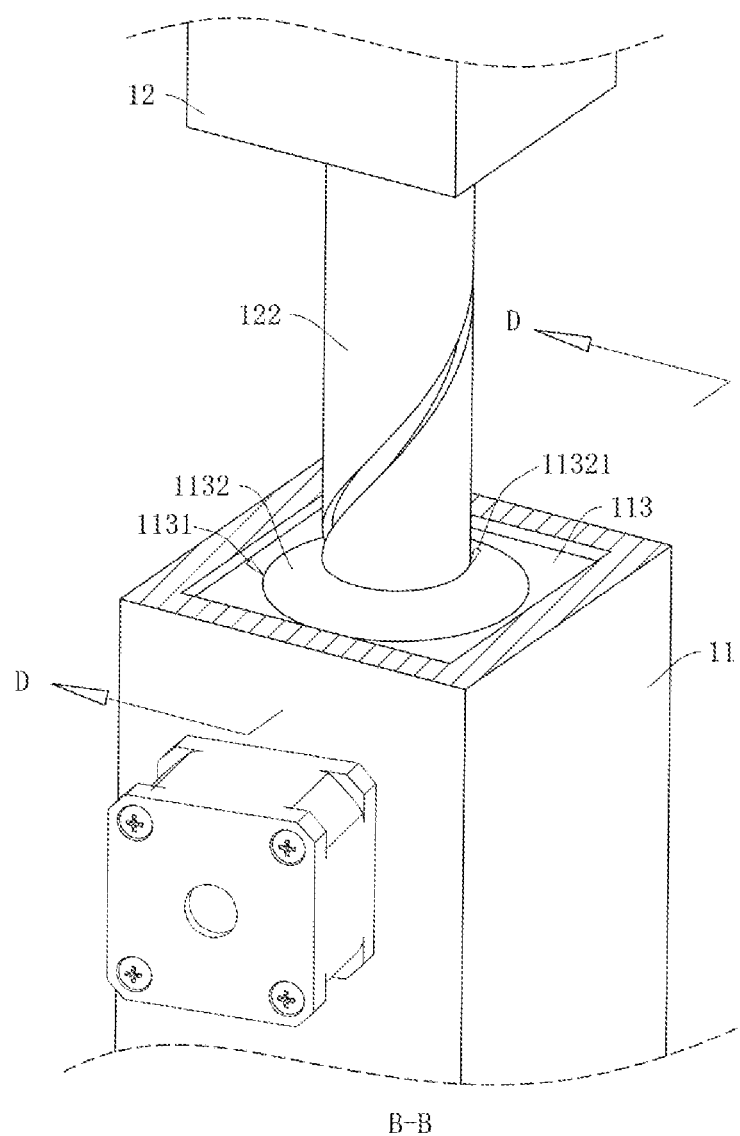
FIG. 9 is a section view of the portable three-dimensional DR system taken from B-B in FIG. 8.

As shown in FIG. 3 and FIG. 8, the difference between the embodiment 1 and embodiment 2 is that the support tube 11 and the support pole 12 of this embodiment are square structure, and an end of the support pole 12 far from the support tube 11 is connected with the mounting platform 121 through the screw, and the mounting platform 121 of this embodiment is square. As shown in FIG. 8 and FIG. 9, the inner wall of the support tube 11 is connected with a support panel 113, and the support panel 113 is provided with the mounting hole 1131, the support panel 113 is further provided with a rotary panel 1132, the rotary panel 1132 of this embodiment is circular structure, the mounting panel 33 is rotatably connected with the support panel 113 by being provided in the support hole 1131, and the center of the mounting panel 33 is further provided with a rotary hole 11321. The end of the support pole 12 closing to the rotary panel 1132 is connected with an adjusting pole 122 through the screw, the adjusting pole 122 is provided with thread, and an end of the adjusting pole 122 far from the support pole 12 is threadedly connected with the rotary panel 1132 by passing through the rotary hole 11321.

Figure 10:
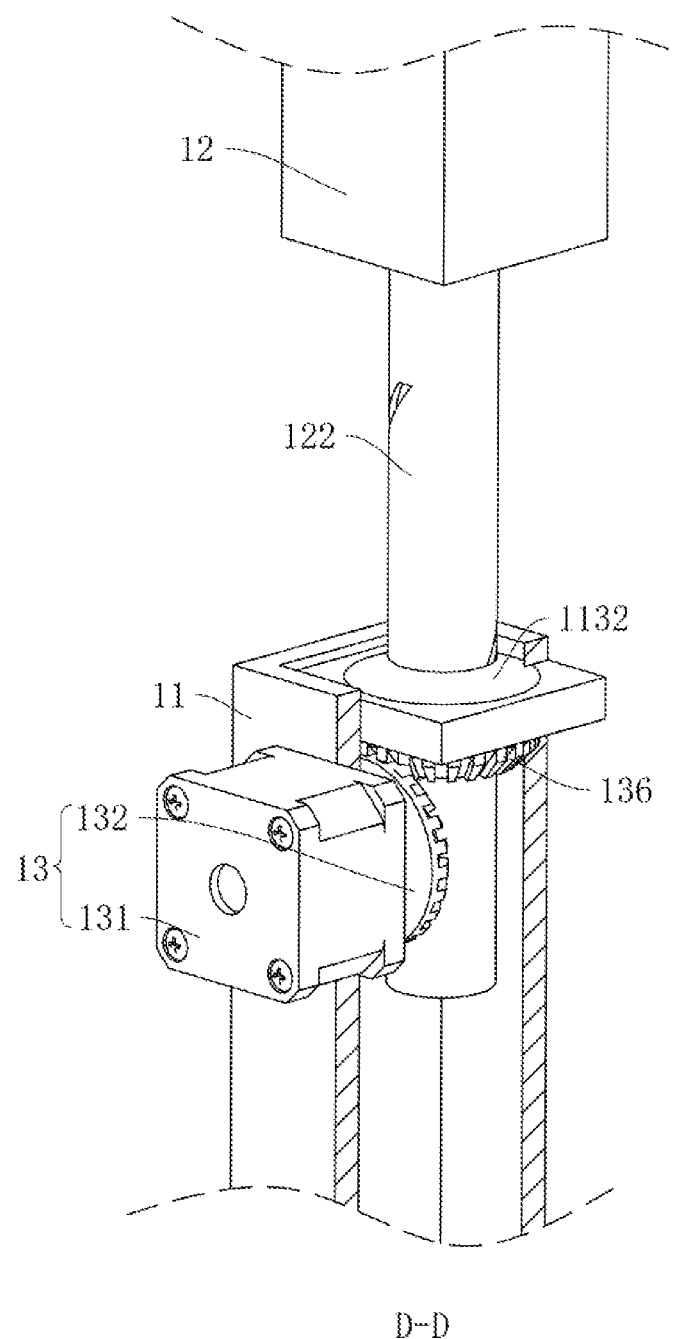
FIG. 10 is a section view of the portable three-dimensional DR system taken from D-D in FIG. 9.

As shown in FIG. 10, the transmission component 13 includes a transmission motor 131, a first bevel gear 135 and a second bevel gear 136, the transmission motor 131 is connected to the outer wall of the support tube 11 through the screw, and an output shaft of the transmission motor 131 is passed through the outer wall of the support tube 11 to be coaxially connected with the first bevel gear 135, this embodiment is in the screw connection. The second bevel gear 136 is connected to an end of the rotary panel 1132 far from the support pole 12 through the screw, an axis of the second bevel gear 136 is coincided with an axis of the adjusting pole 122, and the first bevel gear 135 is engaged with the second bevel gear.

The implementation principle of the embodiment 2 is: when using the portable three-dimensional DR system, the support tube 11 is put on the horizontal plane, and the cover 56 of the mounting box 5 is opened to place the locking pin 55 in the locking hole 1212, the mounting box 5 is connected to the mounting platform 121, and then the mounting cover 52 is opened to adjust the position of the X-ray generator, so that the human body or the object is convenient to be scanned and photographed.

The support-protection pole 34 is possibly to be rotated to land the caster 341, then the mounting pole 32 is pulled out from the mounting tube 31 and the placing panel 322 is fixed on the fixing ring 321, the position of the fixing ring 321 on the mounting pole 32 is adjusted to improve the scope of application and then the flat panel detector 4 is placed on the placing panel 322.

Lastly, the human body or the object is placed in front of the flat panel detector 4, then the transmission motor 131 is controlled through the computer to drive the first bevel gear 135 to rotate by the worker, the first bevel gear 135 is engaged with the second bevel gear 136 to rotate the second bevel gear 136 and the rotary panel 1132 is also driven to rotate, the adjusting pole 122 is driven by the rotary panel 1132 to slide on the rotary panel 1132, the X-ray generator 2 is driven to repeatedly move in the direction of closing to or far from the support tube 11 through the adjusting pole 122, at the same time, the drive motor 141 is started, the rotary wheels 143 on the two sides of the X-ray generator 2 are driven by the drive motor 141, so that the two sides of the X-ray generator 2 can be driven to rotate simultaneously, then the human body or the object is convenient to be scanned and photographed.

Embodiment 3

Figure 11:
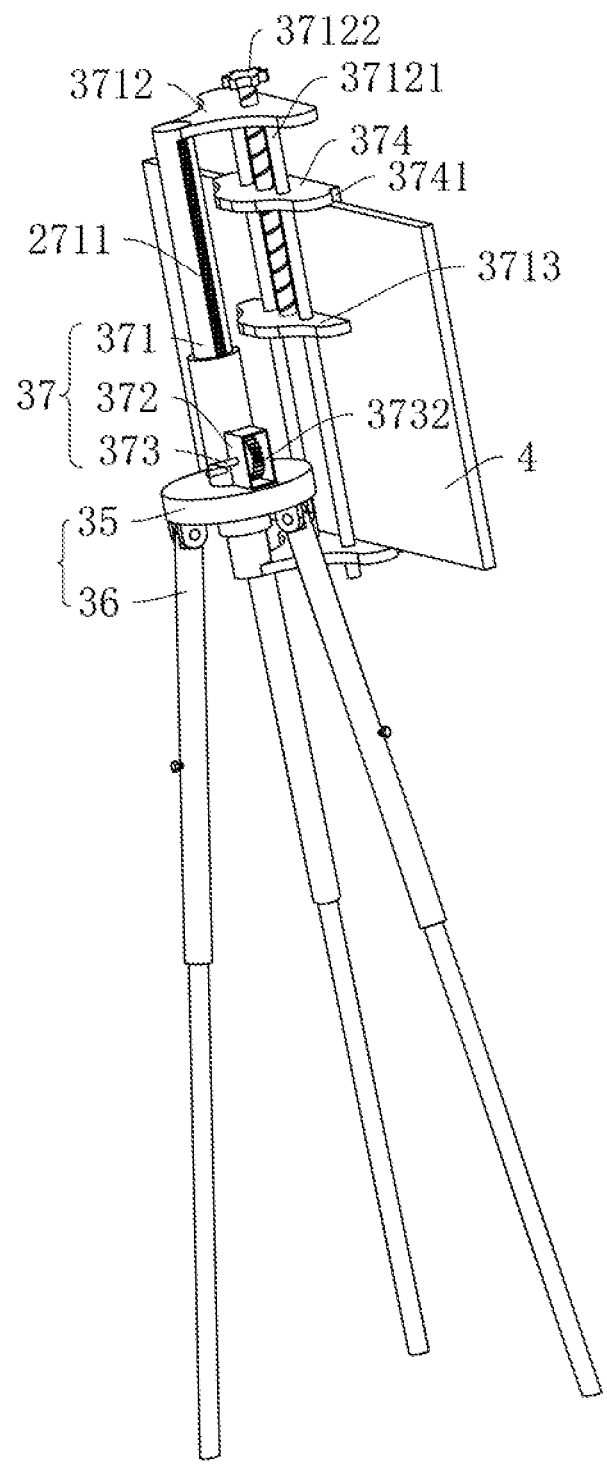
FIG. 11 is a schematic partial structural view of a stand of the portable three-dimensional DR system according to embodiment 3 of the present disclosure.

As shown in FIG. 11, the difference between embodiment 3 and other embodiments is that the stand 3 includes a stand body 35 and a telescopic foot 36, the stand body 35 of this embodiment is of a circular structure, the telescopic foot 36 of this embodiment is of a telescopic structure, and the quantity of the telescopic foot 36 can be plural, and the quantity of the telescopic foot 36 in this embodiment is three. An end of the telescopic foot 36 is hinged with the stand body 35, and another end of the telescopic foot 36 is used for being placed on the horizontal plane.

The stand body 35 is further provided with an adjusting component 37, the adjusting component includes an adjusting bar 372, a moving pole 371 and a rotary pole 373, the adjusting bar 372 is of a hollow structure, and the adjusting bar 372 is connected with an end of the stand body 35 far from the telescopic foot 36. The stand body 35 is provided with an adjusting hole, an end of the moving pole 371 is passed through the adjusting bar 372 and the adjusting hole to be slidingly connected with the stand body 35, and the moving pole 371 is provided with a moving rack 3711. An end of the rotary pole 373 is passed through a sidewall of the adjusting bar 372 and coaxially connected with a rotary gear 3732, an end of the rotary gear 3732 far from the rotary pole 373 is rotatably connected with the inner wall of the adjusting bar 372, and the rotary gear 3732 is engaged with the moving rack 3711. The end of the rotary pole 373 far from the adjusting bar 372 is connected with a handle 3731 for facilitating the worker to hold and to rotate the rotary pole 373.

Two ends of the moving pole 371 is connected with a moving panel 3712 through the screw, and the two moving panels 3712 are relatively arranged in parallel. A guide rod 37121 is provided between the two moving panel 3712, the quantity of the guide rod 37121 in this embodiment is two and the two guide rods 37121 are parallel. The adjusting component 37 further includes a baffle 374, the quantity of the baffle 374 in this embodiment is two, one of the baffles 374 is connected with the moving panel 3712 through the screw, another baffle 374 is slidingly connected with the guide rod 37121 by being passed through by the guide rod 37121, and the baffle 374 is slid in the direction of closing to or far from the another baffle 374. The guide rod 37121 is further provided with a fixing panel 3713, this embodiment is in a screw connection. The moving panel 3712 is further provided with an adjusting bolt 37122 for adjusting the sliding distance of the baffle 374, and an end of the adjusting bolt 37122 far from a nut is sequentially passed through the moving panel 3712 and the baffle 374, and the adjusting bolt 37122 is rotatably connected with a side of the fixing panel 3713, the baffle 374 is threadedly connected with the adjusting bolt 37122. The adjusting bolt 37122 can be rotated to slide the baffle 374 on the guide rod 37121. A limiting panel is integrally formed on the baffle 374, the flat panel detector 4 is provided between the two baffles 374 and is attached to the limiting panel 3741.

The implementation principle of the embodiment 3: when using the portable three-dimensional DR system, the support tube 11 is placed on the horizontal plane, then the cover 56 of the mounting box 5 is opened to place the locking pin 55 in the locking hole 1212, the mounting box 5 is connected to the mounting platform 121, and then the mounting cover 52 is opened to adjust the position of the X-ray generator 2, which is convenient to scan and photograph the human body or the object.

The length of the telescopic foot 36 is adjusted and the telescopic foot 36 is placed on the horizontal plane, then the adjusting screw is rotated to place the flat panel detector 4 between the two baffle 374, and the adjusting screw is rotated again so that the two baffles 374 are attached with the flat panel detector 4 for fixing the flat panel detector 4. Then the rotary pole 373 is rotated to slide the moving pole 371 on the stand body 35, the height of the flat panel detector 4 is adjusted to improve the scope of application.

Lastly, the human body or the object is placed in front of the flat panel detector 4, then the transmission component 13 is controlled through the computer by the worker to drive the X-ray generator 2 to repeatedly move in the direction of closing to or far from the support tube 11, meanwhile, the X-ray generator 2 is driven by the drive component 14 to rotate, so that the human body or the object is convenient to be scanned and photographed.

The above are only some embodiments of the present disclosure, and do not limit the scope of the present disclosure thereto. Therefore, all equivalent changes made according to the structure, shape and principle of the present disclosure shall be included in the scope of the present disclosure.

What is claimed is:

1. A portable three-dimensional digital radiography (DR) system, comprising:
    an X-ray generator;
    a stand placed on a horizontal plane;
    a flat panel detector provided on the stand; and
    a support mechanism comprising:
    a support tube;
    a transmission component for driving the X-ray generator to move towards or away from the support tube;
    a drive component for driving the X-ray generator to rotate; and
    a support pole slidingly provided in the support tube, and wherein the X-ray generator is detachably provided on the support pole; and
    the transmission component comprises:
    a transmission motor provided in the support pole;
    a transmission gear; and
    a transmission rack provided on an inner wall of support tube,
    wherein the transmission motor is connected with the transmission gear, the transmission rack is provided in a length direction of the support tube, the transmission gear is engaged with the transmission rack to drive the support pole to slide in the support tube, one end of the support pole far from the support tube is connected with a mounting platform for mounting the X-ray generator, and the mounting platform is detachably connected with the support tube.

2. The portable three-dimensional DR system of claim 1, wherein the support tube comprises a first support tube and a second support tube, the first support pole is slidingly provided in the second support tube, the support pole is a telescopic pole and is slidingly provided in the first support tube, the transmission rack comprises a first rack provided on an inner wall of the first support tube and a second rack provided on an inner wall of the second support tube, and the first rack and the second rack are spliced with each other.

3. The portable three-dimensional DR system of claim 2, wherein:
    a sliding slot is provided on the first support tube, a magnetic plate is provided on the first support tube, the second rack is provided in the sliding slot and magnetically connected with the magnetic plate; and
    an outer wall of the first support tube is provided with a plurality of position balls, an inner wall of the second support tube is provided with a position hole for containing the position ball and a position slot, the position ball is provided in the position slot and slidingly connected with the second support tube.

4. The portable three-dimensional DR system of claim 1, wherein:
    a mounting box is detachably connected on the mounting platform,
    a containing slot is provided on the mounting box,
    a mounting cover for opening or closing the containing slot is further provided on the mounting box,
    the X-ray generator is provided in the containing slot and rotatably connected with the mounting box,
    the drive component comprises a rotary wheel and a drive motor provided on the mounting box for driving the rotary wheel to rotate, and
    the rotary wheel is configured to drive the X-ray generator to rotate.

5. The portable three-dimensional DR system of claim 1, wherein:
    an inner wall of the support tube is rotatably provided with a rotary panel, and a rotary hole is provided on the rotary panel, one end of the support pole is rotatably connected with an adjusting pole, and the adjusting pole is threadedly connected with the rotary panel through a rotary hole,
    the transmission component comprises a transmission motor provided on the support tube, and
    an output shaft of the transmission motor is concentrically connected with a first bevel gear, the rotary panel is connected with a second bevel gear, and the first bevel gear is engaged with the second bevel gear.

6. The portable three-dimensional DR system of claim 1, wherein:
    the support tube is further provided with a support component,
    the support component comprises a support body, a first roller, a connecting plate and a support bar, and
    the support body is connected with an end of the support pole, the first roller is rotatably connected with the support body, the support beam is connected with the support body, an end of the support bar is rotatably connected with the connecting plate, another end of the support bar is rotatably connected with a second roller, and a locking piece for locking the second roller is provided on the support bar.

7. The portable three-dimensional DR system of claim 1, wherein:

the stand comprises a stand body, a plurality of telescopic feet and an adjusting component, one end of the telescopic foot is hinged with the stand body, and another end of the telescopic foot is placed on a horizontal plane, the adjusting component comprises a moving pole, a rotary pole and a rotary gear, the rotary pole is rotatably connected with the stand body, one end of the rotary pole is connected with the rotary gear, and a moving rack is provided on the moving pole, the rotary gear is engaged with the moving rack, and an adjusting hole is provided on the stand body, one end of the moving pole is slidingly connected with the stand body through the adjusting hole, both ends of the moving pole are provided with baffles parallel to each other, one of the baffles is slidingly connected with the moving pole, and the baffle is used for clamping the flat panel detector.

8. The portable three-dimensional DR system of claim 1, wherein:

the stand comprises a mounting tube, a mounting pole, a mounting panel and a plurality of support-protection bars, and the mounting pole is slidingly provided in the mounting tube, a fixing ring is slidingly provided on the mounting pole, the flat panel detector is detachably connected with the fixing ring, one end of the mounting tube far from the flat panel detector is connected with the mounting panel, the mounting panel is rotatably connected with an end of the support-protection bar, and another end of the support-protection bar is rotatably connected with a caster.

* * * * *